(12) United States Patent
Renhed

(10) Patent No.: US 6,918,488 B2
(45) Date of Patent: Jul. 19, 2005

(54) PACKAGING FOR DISPOSABLE ITEMS

(75) Inventor: Per Renhed, Stockholm (SE)

(73) Assignee: Cederroth International AB, Upplands Vasby (SE)

(*) Notice: Subject to any disclaimer, the term of this patent is extended or adjusted under 35 U.S.C. 154(b) by 180 days.

(21) Appl. No.: 10/450,630

(22) PCT Filed: Mar. 7, 2003

(86) PCT No.: PCT/SE03/00385
§ 371 (c)(1),
(2), (4) Date: Jun. 17, 2003

(87) PCT Pub. No.: WO04/000688
PCT Pub. Date: Dec. 31, 2003

(65) Prior Publication Data
US 2004/0232013 A1 Nov. 25, 2004

(30) Foreign Application Priority Data
Jun. 25, 2002 (SE) .................................. 0201950

(51) Int. Cl.[7] .................. B65D 69/00; B65D 71/00; B65D 83/00; B65D 5/00
(52) U.S. Cl. ............... 206/440; 206/233; 206/570; 206/784; 221/65; 229/101
(58) Field of Search ............... 206/494, 495, 206/440, 233, 803, 806, 270, 254, 784, 449, 751, 758, 754–756, 570; 221/65; 247–249; 229/101

(56) References Cited
U.S. PATENT DOCUMENTS

| | | | | |
|---|---|---|---|---|
| 512,011 A | * | 1/1894 | Colgan | 206/254 |
| 1,262,963 A | * | 4/1918 | McCrea | 206/440 |
| 2,353,761 A | * | 7/1944 | Ringler | 229/101 |
| 2,354,239 A | * | 7/1944 | Williamson | 206/273 |
| 2,361,984 A | * | 11/1944 | Williamson | 229/101 |
| 3,828,923 A | * | 8/1974 | Phillips, Jr. | 206/254 |
| 3,899,077 A | * | 8/1975 | Spiegelberg | 206/441 |
| 4,240,548 A | * | 12/1980 | Stio | 206/250 |
| 4,586,605 A | * | 5/1986 | Newsome | 206/267 |
| 4,645,077 A | * | 2/1987 | McLaughlin et al. | 206/449 |
| 4,967,909 A | * | 11/1990 | McKibben | 206/556 |
| 5,333,732 A | * | 8/1994 | Budny et al. | 206/316.1 |
| 6,050,413 A | * | 4/2000 | Benedetti | 206/440 |
| 6,719,128 B2 | * | 4/2004 | Alpern et al. | 206/63.3 |

* cited by examiner

*Primary Examiner*—Mickey Yu
*Assistant Examiner*—J. Gregory Pickett
(74) *Attorney, Agent, or Firm*—Alfred J. Mangels

(57) ABSTRACT

A package for dispensing articles intended for one time use only, such as skin plasters or adhesive bandages, medicaments, and disposable handkerchiefs, where the articles are placed on top of each other, or on top of and side-by-side of each other, to form a layer of juxtaposed articles. The package includes an upper part and a lower part that is partially telescopically received within the upper part. The lower part of the package is generally rectangular in cross-section and is closed at its bottom and along its sides to form a pocket. The rear wall of the lower part connects with the front edge of a flat panel defining a top wall of the upper part. A tongue extends from the front edge of the upper part down between the respective rear wall and front wall of the lower part of the unit.

10 Claims, 2 Drawing Sheets

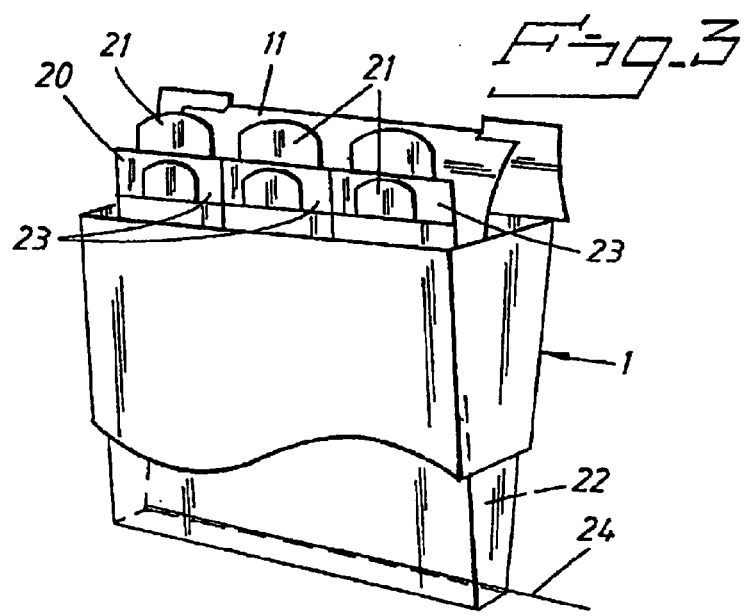
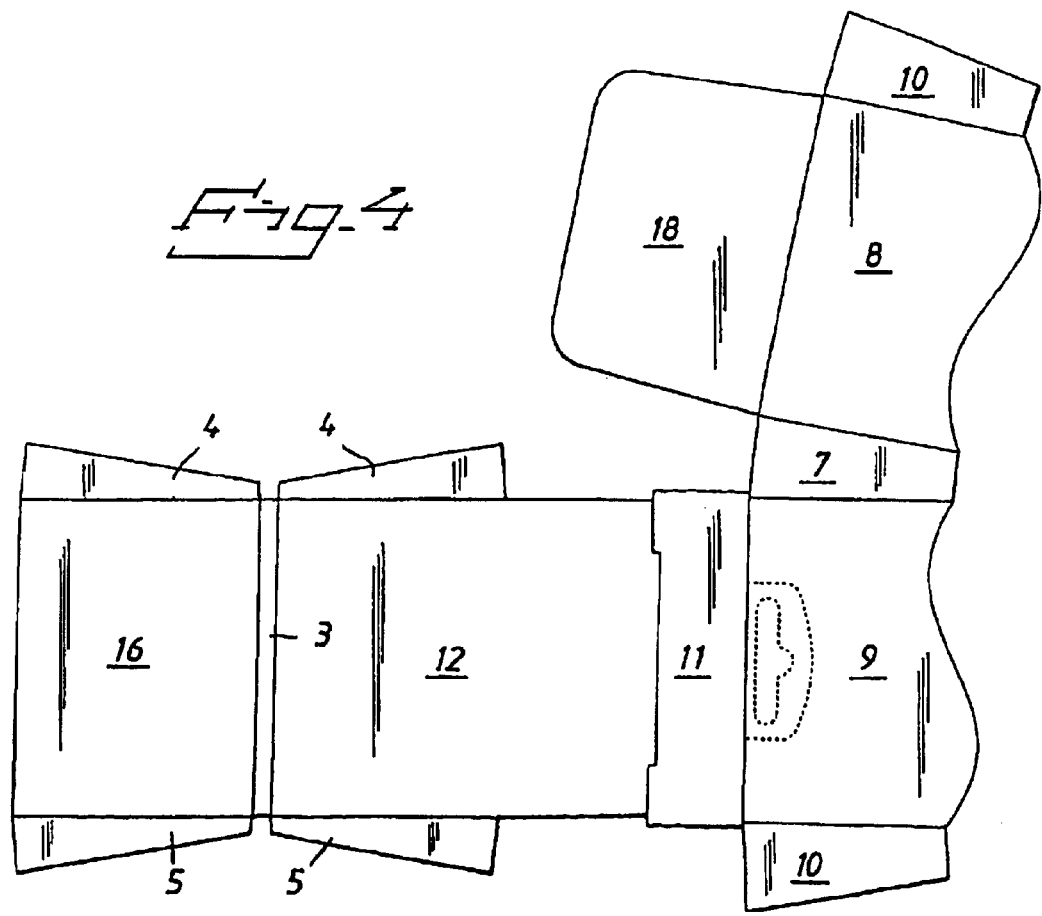

PACKAGING FOR DISPOSABLE ITEMS

BACKGROUND OF THE INVENTION

1. Field of the Invention

The present invention relates to a packaging unit for disposable articles, and more particularly to the packaging of articles of the kind to be protected prior to use while, at the same time, being readily accessible when needed. Examples of such articles include skin plasters or adhesive bandages, medicines, disposable handkerchiefs, cotton wool tops, etc.

The present invention is thus not limited to any specific article, but will be described in the following with reference to skin plasters as an example of the article.

2. Description of the Related Art

A number of plaster packaging units are commercially available. A typical package is comprised of normal thin paper board in which the plasters lie singly in sealed bags. When needing to use a plaster, the cardboard packing unit is opened along one end and a bag containing a plaster is withdrawn from the packaging. Thereafter one end of the bag is opened and the plaster is withdrawn from the bag, this plaster being ready for use.

When kept in a handbag, back pack, or some corresponding carrier, a packaging unit of this nature is easily deformed so as to be either completely or partially open, due to the mechanical weakness of an open cardboard packaging unit. Thus, the cardboard packaging unit cannot be properly resealed. Moreover, the plastic bags tend to become dirty when kept for a long time in an open cardboard unit in a handbag.

Accordingly, an object of the present invention is to provide a closed and resealable plaster packaging unit that contains skin plasters in sealed bags and that can be readily opened to enable a plaster to be removed from said unit. Another object is to provide a packaging unit that is durable against long term storage, for instance in a handbag, and that is also moisture repellent.

These objectives are achieved by means of the present invention.

SUMMARY OF THE INVENTION

The present invention thus relates to a packaging unit for articles intended for one time use only, i.e., disposable articles, such as skin plasters or adhesive bandages, medicaments and disposable handkerchiefs, etc., and where said articles are placed on top of each other, or on top of and side-by-side to each other, or only side-by-side to each other, to form a layer of juxtaposed articles. In cross-section the lower part of the packaging unit is generally rectangular and is closed at its bottom and along its sides so as to form a pocket. The packaging unit includes an upper part that has four sides which are also generally rectangular and which are placed outside the upper half of the lower part of the unit. The upper part is closed at its upper end by a generally flat panel, wherein in the closed state of the packaging unit the upper part of the packaging unit overlaps the upper portion of the lower part of said unit and projects out upwardly from said lower portion. The rear wall of the lower part connects with the front edge of said flat panel. A tongue protrudes from the front edge of the upper part down between the respective rear wall and front wall of the lower part of the unit. The lower part is telescopically moveable into said upper part through a limited distance that is determined by abutment of the bottom edge of the tongue with the bottom wall of the lower part of said packaging unit.

BRIEF DESCRIPTION OF THE DRAWINGS

The invention will now be described in more detail partly with reference to an embodiment of the invention shown in the accompanying drawings, in which

FIG. 3 is a view similar to that of FIG. 2 but showing disposable articles in said unit; and FIG. 4 shows a punched-out sheet prior to the sheet being formed into an inventive packaging unit.

DESCRIPTION OF THE PREFERRED EMBODIMENTS

Figure 1:
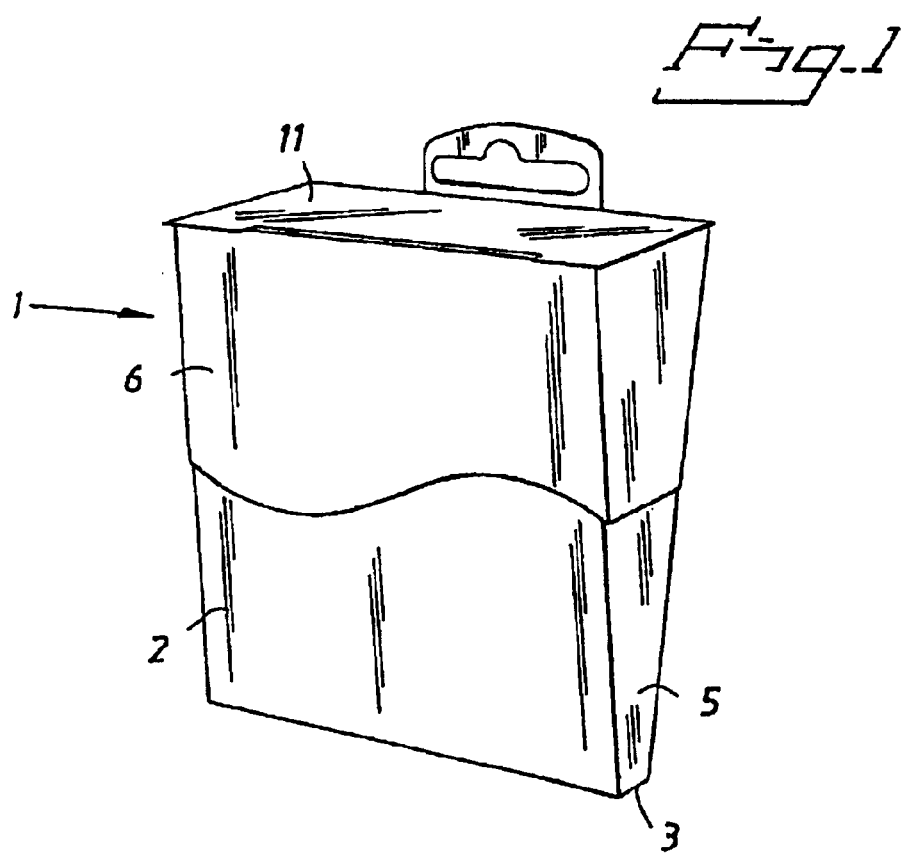
FIG. 1 is a perspective view of a closed packaging unit.

Shown in FIG. 1 is an inventive disposable article packaging unit, e.g., for articles such as skin plasters or adhesive bandages, medicaments, and disposable handkerchiefs.

The articles are enclosed in an elongate, sealingly-closed bag, with the articles placed on top of and side-by-side to each other to form an ordered array consisting of juxtaposed article layers; see FIG. 3.

FIG. 3 shows an open packaging unit with the articles partially protruding up out of the unit.

According to the present invention, the lower part 2 of the packaging unit 1 has a generally rectangular cross-sectional shape and is closed at its bottom 3 and along its sides 4, 5 so as to form a pocket. The packaging unit also includes an upper part 6 that has four sides 7–10, which are also generally rectangular and which are placed outside the upper half of the lower part 2 of said unit. The upper part 6 of the unit is closed at its upper end by a generally flat panel 11. The lower and upper parts of the illustrated embodiment are slightly V-shaped. That shape is intended to include a generally rectangular shape.

When the packaging unit is closed, the upper part 6 of the unit overlaps the upper portion of the lower part 2 of said unit and projects up from the lower part, as evident from FIG. 1.

Figure 2:
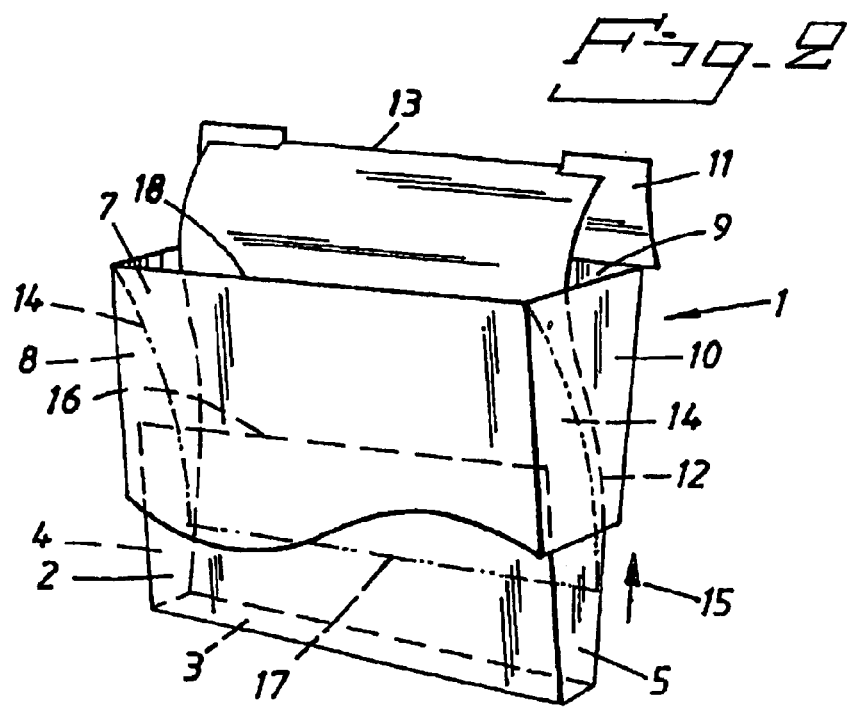
FIG. 2 is a perspective view of an open packaging unit in the absence of disposable items.

It will be seen from FIG. 2 that the rear wall 12 of the lower part 2 connects with the front edge 13 of said flat panel 11. The rear wall 12 is shown both in full lines and in broken lines. A tongue 14 extends from the front edge 18 of the upper part 6, down between respective rear and front walls 12 and 16 of the lower part 2. The tongue 14 is shown in dashed lines.

As indicated by arrow 15, the lower part 2 of the unit can be moved telescopically into the upper part 6 to a limited extent, determined by abutment of the bottom edge 17 of the tongue 14 with the wall that forms bottom 3 of the lower part 2 of the unit.

The lower part 2 of the unit can be inserted into its upper part 6 telescopically, so that said lower and upper parts will essentially overlap each other.

According to one preferred embodiment, the packaging unit is made of a springy plastic material.

It is also preferred that the packaging unit is made of a material which is both rigid and resilient, such as polypropylene.

This means that the packaging unit will be held closed by the inherent spring forces that are generated in response to the arcuate shape taken by the rear wall 12, evident from FIG. 2, when the unit is opened, i.e. when the lower part 2 is pushed into the upper part 6. An open packaging unit is re-sealed or closed, by pulling down the lower part 2 of the unit, where with separation of the upper and lower parts ceases when the flat portion 11 comes into abutment with the top edges of the upper part 6.

According to one preferred embodiment, the packaging unit is punched out of apiece of material and then folded into its final configuration. FIG. 4 illustrates a punched-out sheet prior to folding the sheet to form said packaging unit. Those reference numerals used to identify the unit parts in FIG. 2 have been used in FIG. 4 to identify corresponding parts.

According to one highly preferred embodiment, the array 20 of disposable articles 21 is pushed down into pocket 22 defined by lower part 2, and each article is held, either directly or indirectly, in the unit 1 in close proximity to the lower part of the pocket 22, as shown in FIG. 3. When the packaging unit is closed, each of the articles projects out of the pocket in its longitudinal direction, up to said flat panel 11 of the upper part of the packaging unit.

According to one preferred embodiment the articles 21 are packaged in bags 23 that are welded, glued, or stapled to the lower part 2 of the packaging unit 1. This can be effected along the marked line 24, as seen in FIG. 3.

The packaging unit is particularly suited for use with skin plasters or adhesive bandages, as illustrated in FIG. 3.

According to one preferred embodiment the sealingly closed bags 23 are divided in two, into a top and a bottom section, transversely to the long axis of the article, and slightly below the free end of the article.

According to another much preferred embodiment there is provided between said top and bottom sections of respective bags a joint which functions to cause the top section to separate from the bottom section when a user opens the packaging unit, by pushing the lower part into the upper part, and pulls on the top section of the bag 23. Attachment of the bag to the bottom 3 of the lower part 2 is such that the affixed bottom section of the bag 23 will remain in the packaging unit 1.

It will thus be obvious that the present invention solves the problems mentioned in the introduction.

Although the invention has been described with reference to a number of embodiments thereof, it will be understood that the structural design of the various parts and components can be varied without changing the function of the packaging unit.

Consequently, the present invention shall not be considered to be limited to the described and illustrated embodiments thereof, since variations can be made within the scope of the accompanying claims.

What is claimed is:

1. A packaging unit for disposable articles intended for one time use only, where said articles are placed in one or more layers of juxtaposed articles, said packaging unit comprising: a lower part of generally rectangular cross section and closed at its bottom and along its sides as to form a pocket, an upper part that has four sides that define a generally rectangular cross section and which are placed outside an upper portion of the lower part of the unit, wherein said upper part is closed at its upper end by a generally flat panel, wherein in the closed state of the packaging unit the upper part of the packaging unit at least partially overlaps the upper portion of the lower part of said unit and extends upwardly from said lower part, wherein a rear wall of the lower part connects with a front edge of the flat panel of the upper part, wherein a tongue extends from a front edge of the upper part down between the rear wall and a front wall of the lower part of the unit, and wherein the lower part is telescopically moveable relative to said upper part through a limited distance determined by abutment of a bottom edge of the tongue with the bottom of the lower part.

2. A packaging unit according to claim 1, wherein the packaging unit is formed from a resilient plastic material.

3. A packaging unit according to claim 2, wherein the packaging unit is formed from a rigid and resilient plastic material.

4. A packaging unit according to claim 1, wherein the packaging unit is punched from a piece of material and then folded into its final state.

5. A packaging unit according to claim 1, wherein the articles are in respective bags positioned in said pocket and each of the bags is affixed in the packaging unit close to the bottom portion of the pocket; and wherein each of the bags is within the pocket in the direction of its long axis when the packaging unit in its closed state.

6. A packaging unit according to claim 1, wherein the articles are each sealingly enclosed in an elongate bag which is divided into two sections, a top section and a bottom section, transversely to a long axis of the article and slightly below the free an end of the article.

7. A packaging unit according to claim 6, including a joint between said top and bottom sections of respective articles, which joint functions to cause the top section of an article to separate from its bottom section when a user opens the packaging unit by pushing the lower part into the upper part to extend an article from the upper part and pulls on the top section of the article, wherewith attachment of the article to the bottom of the lower part is such that the affixed bottom section of the bag will remain in the packaging unit.

8. A packaging unit according to claim 5, wherein the articles are secured to the lower part of the packaging unit.

9. A packaging unit according to claim 1, wherein the articles are skin plasters.

10. A packaging unit according to claim 3, wherein the plastic material is polypropylene.

* * * * *